United States Patent [19]

Dillard et al.

[11] 4,100,280

[45] Jul. 11, 1978

[54] 1,3-DIALKYL-6,7-METHOXY-1H-1,2,4-BEN-ZOTHIADIAZINE-1-OXIDES

[75] Inventors: Robert D. Dillard, Zionsville; Donald E. Pavey, Bargersville, both of Ind.

[73] Assignee: Eli Lilly and Company, Indianapolis, Ind.

[21] Appl. No.: 822,465

[22] Filed: Aug. 8, 1977

[51] Int. Cl.² .................. C07D 285/24; A61K 31/38; A61K 31/54
[52] U.S. Cl. ........................ 424/246; 544/12
[58] Field of Search ........................... 544/12; 424/246

[56] References Cited

U.S. PATENT DOCUMENTS

| 3,933,805 | 1/1976 | Cohnen | 544/12 |
| 4,022,774 | 5/1977 | Sowinski et al. | 544/12 |

*Primary Examiner*—John M. Ford
*Attorney, Agent, or Firm*—James L. Rowe; Arthur R. Whale

[57] ABSTRACT

1,3-Dialkyl-6,7-methoxy-1H-1,2,4-benzothiadiazine-1-oxides, useful as hypotensive agents.

8 Claims, No Drawings

1,3-DIALKYL-6,7-METHOXY-1H-1,2,4-BENZO-THIADIAZINE-1-OXIDES

BACKGROUND OF THE INVENTION 1,2,4-Benzothiadiazine-1-oxides are known in the art. For example, U.S. Pat. No. 3,936,977 discloses 1-phenyl (or substituted phenyl)-1H-1,2,4-benzothiadiazine-3(4H)-ones bearing a substituent on the N-3 nitrogen and permissible substituents in the phenyl ring of the benzothiadiazine including alkoxy. The compounds disclosed therein are stated to be central nervous system depressants and diuretics. The corresponding 1-oxides are disclosed in Derwent 32823w. U.S. Pat. No. 3,957,769 discloses 1-phenyl (or substituted phenyl) 3-amino (or alkylamino or dialkylamino)-1H-1,2,4-benzothiadiazine-1-oxides which may be substituted in the phenyl ring of the benzothiadiazine with, among other groups, an alkoxy group. These compounds are also said to be central nervous system depressants and diuretics. U.S. Pat. No. 3,933,805 discloses 1-phenyl (or substituted phenyl) 3-dialkylaminomethyl-1H-1,2,4-benzo-thiadiazine-1-oxides permissibly substituted with methoxy in the phenyl ring of the benzothiadiazine molecule. The compounds are said to be anti-hypertensives. Stoss and Satzinger, Chem. Ber., 109, 2097 (1976) prepared 1-phenyl or 1-methyl-3-amino-1H-1,2,4-benzothiadiazine-1-oxides containing a methyl or chloro substituent in the benzene ring portion of the benzothiadiazine ring. Cohnen and Mahnke, Chem. Ber., 105, 757, (1972) described on page 758, compund 7jA which is 1-phenyl-3-methylaminomethyl-7-chloro-1H-1,2,4-benzothiadiazine-1-oxide. The compounds described therein were employed as intermediates for the preparation of Librium-like drugs.

PRIOR ART 1,3,6-Trimethyl-1H-1,2,4-benzothiadiazine-1-oxide and 1,6-dimethyl-1H-1,2,4-benzothiadiazine-1-oxide, are disclosed as new ring systems containing chiral sulfur by Williams and Cram in papers appearing in J. Am. Chem. Soc., 93 733 (1971) and J. Org. Chem., 38, 20 (1973). No utility is disclosed therein for any of the compounds. Several 1-(substituted phenyl)-3-(chloromethyl or methyl or dimethylaminomethyl)-1H-1,2,4-benzothiadiazine-1-oxides bearing a permissible chlorine or nitro at 7 have been prepared according to Ber., 105, 757 (1972). 1,3-dialkyl-6,7-dimethoxy-1H-1,2,4-benzothiadiazine-1-oxides have not been disclosed, either generically or specifically, in the prior art.

SUMMARY OF THE INVENTION

This invention provides 1,3-dialkyl-6,7-dimethoxy-1H-1,2,4-benzothiadiazine-1-oxides of the formula:

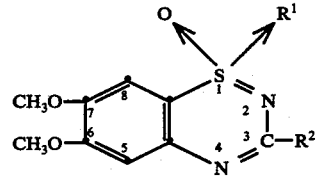

wherein $R^1$ and $R^2$ are individually $C_1$-$C_3$ alkyl, and pharmaceutically acceptable acid addition salts thereof.

In the above formula, when $R^1$ or $R^2$ is $C_1$-$C_3$ alkyl, they can be methyl, ethyl, isopropyl, or n-propyl.

The pharmaceutically acceptable acid addition salts of this invention include salts derived from inorganic acids such as: hydrochloric acid, nitric acid, phosphoric acid, sulfuric acid, hydrobromic acid, hydriodic acid, nitrous acid, phosphorous acid and the like, as well as salts derived from nontoxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

Illustrative bases coming within the scope of this invention include:
1-ethyl-3-methyl-1H-1,2,4-benzothiadiazine-1-oxide,
1-isopropyl-3-ethyl-1H-1,2,4-benzothiadiazine-1-oxide,
1-n-propyl-3-ethyl-1H-1,2,4-benzothiadiazine-1-oxide,
1-n-propyl-3-isopropyl-1H-1,2,4-benzothiadiazine-1-oxide,
1-ethyl-3-n-propyl-1H-1,2,4-benzothiadiazine-1-oxide,
1-methyl-3-n-propyl-1H-1,2,4-benzothiadiazine-1-oxide and the like.

The compounds of this invention, either as such are in the form of an acid addition salt thereof are useful in lowering blood pressure. Although they demonstrate this useful activity in the laboratory in both normotensive and spontaneously hypertensive mammals, the compounds would be employed to lower blood pressure of mammals having an elevated blood pressure. Thus, this invention also provides a method of lowering blood pressure in a mammal, by administering to a mammal having an elevated blood pressure and in need of treatment a hypotensive dose of a compound according to the above formula. The pharmaceutically acceptable salts of these compounds are, of course, equally useful in treating mammalian hypertension.

In carrying out the therapeutic method of the present invention, it is generally preferred to employ a composition comprising the active agent and one or more adjuvants suited to the particular route of administration. Compositions for oral administration may be either solid; e.g., capsules, tablets, pills, powders, etc., or liquid; e.g., emulsions, solutions, suspensions, syrups, elixirs, etc. combined with conventional adjuvants. In the case of solid formulations, suitable adjuvants include inert substances such as sucrose, lactose, and starch. In the case of liquid formulations, suitable adjuvants include water, mineral oil, etc. When an aqueous solution is desired, an acid addition salt is conveniently employed. Either solid or liquid formulations can include lubricating agents, wetting agents, emulsifying and suspending agents, preserving agents, sweetening agents or flavoring agents.

In the instance of parenteral administration, the compounds of the present invention are formulated in a suitable sterile, injectable liquid. For example, a pharmaceutically-acceptable acid-addition salt formed with a non-toxic acid is used in an isotonic salt solution for I.V. or other injection route. Oral administration is generally preferred. An acceptable formulation for oral use is a pharmaceutical preparation in dosage unit form adapted for administration to obtain a hypotensive effect, comprising, per dosage unit, an effective non-toxic amount within the range from about 0.01 to about 100 milligrams of one or more of the compounds of this invention.

The compounds of this invention are prepared according to the following reaction scheme:

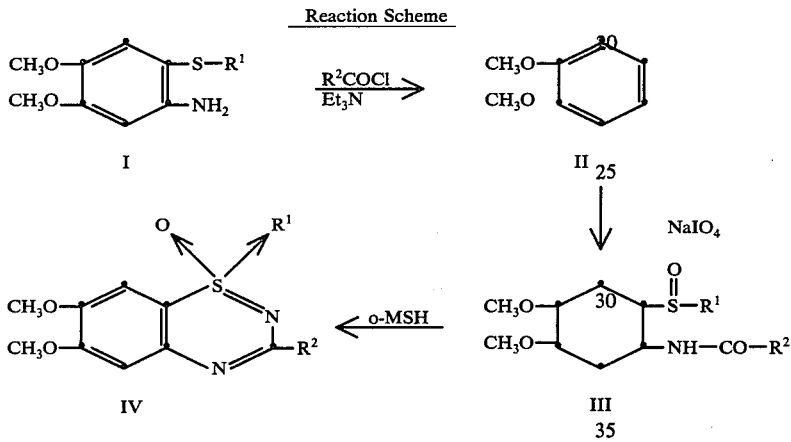

In the above Reaction Scheme, $R^1$ and $R^2$ are as before, individually $C_1$-$C_3$ alkyl. In carrying out the reactions symbolically illustrated therein, a 2-alkylthio-4,5-dimethoxyaniline (I) is acylated with a lower alkanoyl halide or anhydride in the presence of -dimethoxy-1H-1,2,4-benzothiadiazine-1-oxides acid acceptor such as triethylamine, solid sodium carbonate or the like in an inert solvent. Suitable inert solvents include chlorinated hydrocarbons such as chloroform, methylene dichloride, dichloroethylene, etc. and aromatic hydrocarbons such as benzene, toluene, and xylene. The product of this reaction is a 2-alkylthio-4,5-dimethoxyacetanilide or propionanilide or butyranilide (II). Oxidation of this compound, as with sodium periodate or other oxidizing agents of similar oxidation potential including permanganate, peracids, etc., yields the corresponding 2-alkylsulfinyl derivative (III). Treatment of III with o-mesitylenesulfonylhydroxylamine (o-MSH) effects a cyclization to yield the desired 1,3-dialkyl-6,7-dimethoxy- of this invention (IV), which are conveniently purified in the form of an acid addition salt thereof.

Compounds having a 1-alkyl-1H-1,2,4-benzothiadiazine-1-oxide ring system, such as the compounds of this invention contain an assymetric center. This center is the chiral tetrahedral sulfur atom, attached to four different groups, including the oxide group. Resolution of such chiral molecules into optically-active enantiometers can be accomplished by procedures available from the art.

Structure IV in the above Reaction Scheme represents both enantiomers resulting from the chiral sulfur atom present therein. It is not known whether one or both enantiomers has the pronounced hypotensive activity found for these compounds and a racemate containing one or more active enantiomers is also useful as a hypotensive agent.

This invention is further illustrated by the following specific examples.

EXAMPLE 1

Preparation of 3-Bromo-4-nitroveratrole 100 g. of 4-bromoveratrole were added in dropwise fashion with stirring to 750 ml. of nitric acid (Sp. Gr. 1.42) over a 40 minute period. The temperature was maintained in the range −8° to −4° C. with external cooling consisting of an ice-ethanol bath. After the addition had been completed, the stirring was continued for another 10 minutes with cooling. 3-Bromo-4-nitroveratrole formed in the above reaction precipitated after diluting the reaction mixture with 2500 ml. of water. The precipitate was separated by filtration, and the filter cake washed with water. Recrystallization of the filter cake from about 2.5 l. of ethanol yielded 3-bromo-4-nitroveratrole, a light yellow product, which melted at 120°–122° C. Yield = 83.4 g.

Analysis Calc.: C, 36.67; H, 3.08; N, 5.34; Found: C, 36.44; H, 3.05; N, 5.97.

EXAMPLE 2

Preparation of 3-Methylthio-4-nitroveratrole

A reaction mixture containing 21 g. of potassium carbonate, 25 g. of methanethiol and 30 ml. of ethanol was cooled in an ice-water bath. 33.5 g. of 3-bromo-4-nitro-veratrole were added thereto. The reaction mixture was stirred for 1 hour under cooling and was then allowed to warm up to ambient temperature, at which temperature it was stirred for an additional 24 hours. 3 l. of water were then added and the resulting precipitate of 3-methylthio-4-nitroveratrole formed in the above reaction was separated by filtration. The filter cake was recrystallized from a benzene-ethanol solvent mixture to yield yellow crystals melting at 137°–140° C. (weight = 22.8 g)

Analysis Calc.: C, 47.15; H, 4.84; N, 6.11; Found: C, 47.38; H, 4.97; N, 6.16.

An additional 3.1 g. of 3-methylthio-4-nitroveratrole were recovered from the mother liquor.

EXAMPLE 3

Preparation of 2-Methylthio-4,5-dimethoxyaniline

A reaction mixture was prepared containing 107.1 g. of 200 mesh metallic tin, 330 ml. of glacial acetic acid, and 50 ml. of 12 N aqueous hydrochloric acid. 68.7 g. of 3-methylthio-4-nitroveratrole were added thereto in 4 portions over a 20 minute period. After the addition had been completed, the reaction temperature had risen to 105° C. An additional 300 ml. of 12 N aqueous hydrochloric acid were added thereto over a 10 minute period. The temperature was maintained in the range 100°–105° C. for about 1.5 hours. The reaction mixture was then cooled in an ice-water bath, made strongly basic with 50 percent aqueous sodium hydroxide and diluted with 5 volumes of water. The aqueous layer was extracted three times with 2 liter portions of ether. The ether extracts were combined, dried, and the ether removed therefrom in vacuo. The resulting residue comprising 2-methylthio-4,5-dimethoxyaniline formed in the above reduction melted at 72°–4° C. after recrystallization from a benzene-hexane solvent mixture. Yield = 37 g. An additional 10 g. were obtained from mother liquors.

Analysis Calc.: C, 54.25; H, 6.58; N, 7.03; Found: C, 54.13; H, 6.58; N, 7.05.

EXAMPLE 4

Alternate Preparation of 2-Methylthio-4,5-dimethoxyaniline

A reaction mixture was prepared containing 68.7 g. of 3-methylthio-4-nitroveratrole, 261 g. sodium dithionite ($Na_2S_2O_4$), 1500 ml. of ethanol and 2250 ml. of water. The reaction mixture was heated at reflux temperature for about 1 hour and then cooled. The reaction mixture was then made basic with potassium carbonate and the resulting alkaline solution concentrated in vacuo to one-half its original volume. The aqueous solution was extracted twice with 2 l. portions of ether. The ether extracts were combined, dried, and the ether removed therefrom by evaporation in vacuo. The solid residue, comprising 2-methylthio-4,5-dimethoxy aniline formed in the above reaction, was recrystallized from a benzene-hexane solvent mixture to yield 33.6 g. of crystalline material melting at 69°–72° C.

2-Ethylthio-4,5-dimethoxyaniline, 2-n-propylthio-4,5-dimethoxyaniline, and 2-isopropylthio-4,5-dimethoxyaniline are prepared in analogous fashion by substituting ethanethiol, n-propylthiol and isopropylthiol for methanethiol in Example 2 above to prepare the corresponding 3-alkylthio-4-nitro-veratrole and then reducing the nitrogroup by the procedure of either Example 3 or Example 4.

EXAMPLE 5

Preparation of 2-methylthio-4,5-dimethoxyacetanilide

A solution of 24.1 g. of acetylchloride and 50 ml. of methylene dichloride was added in dropwise fashion to a second solution of 19.9 g. of 2-methylthio-4,5-dimethoxyaniline and 0.15 mole of triethylamine in 500 ml. of methylene dichloride. The second solution had been previously cooled to about 0° C. The reaction mixture was stirred with cooling for about 2 hours and then washed twice with 500 ml. portions of water. The organic layer was separated and dried and the volatile constituents removed therefrom by evacuation in vacuo. The resulting solid residue was recrystallized from a benzene-petroleum ether (boiling point = 60°–71° C.) solvent mixture to yield 18.2 g. of 2-methylthio-4,5-dimethoxy-acetanilide melting at 101°–3° C.

Analysis Calc.: C, 54.75; H, 6.27; N, 5.80 Found: C, 54.97; H, 6.44; N, 5.89

EXAMPLE 6

Preparation of 2-methylsulfinyl-4,5-dimethoxyacetanilide

About 0.058 moles of 2-methylthio-4,5-dimethoxyacetanilide were added to a mixture of 0.06 moles of sodium periodate in 200 ml. of water and 200 ml. of methanol. This latter solution had previously been cooled to about 0° C. The reaction mixture was stirred with cooling for about 8 hours and then at room temprature for an additional 12 hours, and was then diluted with 500 ml. of water. The aqueous layer was extracted with 2,500 ml. portions of chloroform. The chloroform extracts were combined and the combined extracts washed with water and dried. Evaporation of the volatile constituents at reduced pressure yielded a solid, recrystallization of which from a benzene-petroleum ether (b.p. = 60°–71° C) solvent mixture yielded 11 g. of 2-methylsulfinyl-4,5-dimethoxyacetanilide melting at 166°–8° C.

Analysis Calc.: C, 51.35; H, 5.88; N, 5.44 Found: C, 51.09; H, 5.67; N, 5.50

EXAMPLE 7

Preparation of 2-isopropylsulfinyl-4,5-dimethoxyacetanilide

A solution of 6.8 g. of 2-isopropylthio-4,5-dimethoxyaniline and 0.04 moles of triethylamine in 200 ml. of methylene dichloride were cooled to about 0° C. 3.2 g. of acetyl chloride were added thereto in dropwise fashion. The reaction mixture was stirred with cooling for about 2 hours and then washed successively with water, with 100 ml. of 10 percent aqueous sodium hydroxide, with water again, with 100 ml. of 5 percent aqueous hydrochloric acid and finally with water. The reaction mixture was then dried, and the volatile constituents removed in vacuo. A residual oil remained comprising 2-isopropylthio-4,5-dimethoxyacetanilide formed in the above reaction. The residual oil was dissolved in 250 ml. of acetic acid and 3.5 ml. of 31 percent hydrogen peroxide were added thereto. This reaction mixture was stirred for about 6 hours and was then concentrated in vacuo to a residual oil comprising 2-isopropylsulfinyl-4,5-dimethoxyacetanilide formed in the above reaction. The oil was recrystallized from diisopropyl ether to yield 6.3 g. of product melting at 117°–120° C.

Analysis Calc.: C, 54.72; H, 6.71; N, 4.91 Found: C, 54.46; H, 6.68; N, 4.88

EXAMPLE 8

Preparation of 1.3-dimethyl-6,7-dimethoxy-1H-1,2,4-benzothiadiazine-1-oxide

A reaction mixture was prepared containing 0.02 mole of 2-methylsulfinyl-4,5-dimethoxyacetanilide in 0.04 mole of o-mesitylenesulfonylhydroxylamine in 180 ml. of acetonitrile. The reaction mixture was stirred at ambient temperature for about 25 hours and then was concentrated in vacuo to a solid residue. The solid was dissolved in 1 liter of methylene dichloride and the methylene dichloride solution washed with 500 ml. of water containing 25 ml. of 14N aqueous ammonium hydroxide and then with water. The methylene dichloride solution was dried and the methylene dichloride removed therefrom by evaporation in vacuo leaving a solid residue. The solid residue comprising, 1,3-dimethyl-6,7-dimethoxy-1H-1,2,4-benzothiadiazine-1-oxide prepared as above, was dissolved in ethanol and the ethanol solution saturated with anhydrous chloride. The solvent and excess hydrogen chloride were removed in vacuo and the residue, comprising 1,3-dimethyl-6,7-dimethoxy-1H-1,2,4-benzothiadiazine-1-oxide hydrochloride, was recrystallized from ethanol to yield 3.4 g. of product melting at 226°-7° C.

Analysis Calc.: C, 45.44; H, 5.20; N, 9.63 Found: C, 45.20; H, 4.98; N, 9.44

In similar fashion, 2-isopropylsulfinyl-4,5-dimethoxyacetanilide was reacted with o-mesitylenesulfonylhydroxylamine to yield 1-isopropyl-3-methyl-6,7-dimethoxy-1H-1,2,4-benzothiadiazine-1-oxide hydrochloride melting at 195°-7° C.

Analysis Calc.: C, 48.97; H, 6.01; N, 8.79 Found: C, 48.70; H, 6.05; N, 8.60

EXAMPLE 9

Preparation of 1-isopropyl-3-ethyl-6,7-dimethoxy-1H-1,2,4-benzothiadiazine-1-oxide About 0.04 moles of propionyl chloride were added in dropwise fashion to a solution of 0.03 moles of 2-isopropylthio-4,5-dimethoxyaniline and 0.04 moles of triethylamine cooled to about 0° C. The reaction mixture was stirred for 2 hours with cooling and was then washed with water and dried. The volatile constituents were removed under reduced pressure leaving a residual oil comprising 2-isopropylthio-4,5-dimethoxypropionanilide. This residual oil was dissolved in 250 ml. of acetic acid and 3.5 ml. of 31 percent hydrogen peroxide added thereto. The reaction mixture was stirred for 6 hours and then concentrated in vacuo to an oil. The oil was dissolved in methylene dichloride, and the methylene dichloride solution washed with water and dried. Removal of the methylene dichloride in vacuo yielded 7 g. of a hard wax comprising 2-isopropylsulfinyl-4,5-dimethoxypropionanilide formed in the above reaction. The compound was not further purified but was mixed with 0.05 mole of o-mesitylenesulfonylhydroxylamine in 300 ml. of acetonitrile and the subsequent solution was stirred for 72 hours at room temperature. Removal of the volatile constituents in vacuo yielded a solid comprising 1-isopropyl-3-ethyl-6,7-dimethoxy-1H-1,2,4-benzothiadiazine-1-oxide formed in the above reaction. The solid residue was dissolved in one liter of methylene dichloride and the methylene dichloride solution washed with 400 ml. of water containing 40 ml. of 14N ammonium hydroxide and then with water. The methylene dichloride solution was dried, and the solvent removed therefrom in vacuo. The residue comprising 1-isopropyl-3-ethyl-6,7-dimethoxy-1-H-1,2,4-benzothiadiazine-1-oxide in purified form was dissolved in ethanol and the ethanol solution saturated with anhydrous hydrogen chloride. The solvent and excess hydrogen chloride were removed in vacuo yielding 1-isopropyl-3-ethyl-6,7-dimethoxy-1H-1,2,4-benzothiadiazine-1-oxide hydrochloride (4.8 g.) which melted at 199°-201° C. after recrystallization from an ethanol-isopropyl ether solvent mixture.

Analysis Calc.: C, 50.52; H, 6.36; N, 8.42 Found: C, 50.35; H, 6.46; N, 8.36

The compounds of this invention, are hypotensive agents. They manifest this hypotensive activity by demonstrating an ability to reduce the blood pressure of normotensive rabbits. The test procedure employed is as follows:

Male white rabbits weighing approximately 2.5 – 3.5 kg. are used. These animals have chronic indwelling arterial cannulae prepared as follows: The rabbits are anesthetized with secobarbital (30 mg/kg i.v.). An incision is made along the *linea alba* at the approximate level of the bifurcation of the abdominal aorta. A tygon cannula is inserted into the aorta at its bifurcation and anchored so that the tip of the cannula is just distal to the renal artery. The distal end of the cannula is looped, anchored to the posterior abdominal wall, and passed through muscle wall and run subcutaneously rostral, and exteriorized at the nape of the neck. The cannula is kept filled with heparin (1000 units/ml) and, when not in use, is plugged with a stylet. Systolic, diastolic and mean blood pressure in rabbits so prepared is measured by direct recording. The drug under evaluation is administered to the test rabbit at a predetermined dose level with a 0.2 mg/kg. injection volume intravenously via a major ear vein. While the blood pressure is being recorded, heparin is infused through the transducer and into the artery at a rate of 0.01 ml/min. using a Harvard Apparatus infusion pump. This infusion serves two purposes (1) it insures a clot-free period for recording and (2) results in a more stable baseline for pressure recording.

The control period starts 30 min. afater the rabbits have been placed in their stocks. The control values are taken after the 30 minute "accommodation" period. The drug is then administered intravenously and readings taken at set intervals terminating at 120 min. post-dosing. The data are analyzed using a Student *t* test.

In Table 1, which follows, in column 3, there is given the lowest dose level in mg/kg. of rabbit body weight which produced a statistically significant lowering of blood pressure for the drug named in columns 1 and 2.

TABLE 1

$$CH_3O-\text{[benzothiadiazine ring with }R^1\text{ on S, }R^2\text{ on C]} \cdot HCl$$

| $R^1$ | $R^2$ | Hypotensive dose |
|---|---|---|
| Isopropyl | ethyl | 10.0 mg/kg. |
| Isopropyl | methyl | 10.0 mg/kg. |
| methyl | methyl | 12.5 mg/kg. |

EXAMPLE 10

Preparation of salts

Salts and the free bases of this invention are prepared by dissolving the free base in ether and adding an equivalent of a suitable non-toxic acid, for example, maleic acid, also in ether. The salt thus formed, as for example the maleate salt, is insoluble in ether and can be isolated by filtration. Alternatively, the amine base can be dissolved in ethanol and an equivalent of the acid, for example, sulfuric acid, added as an ethanolic solution. In this instance, since the salt thus formed is soluble in the reaction mixture, the salt is isolated by evaporation of the solvent in vacuo. Salts which can be formed by the above procedures include, among others, the hydrochloride, hydrobromide, phosphate, hydrogen phosphate, dihydrogen phosphate, acetate, succinate, tartrate, citrate, benzoate, and p-toluene sulfonate salts.

We claim:

1. A compund of the formula

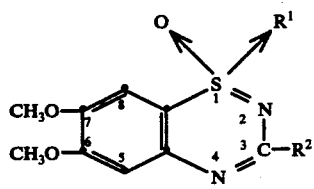

wherein $R^1$ and $R^2$, individually, are $C_1$—$C_3$ alkyl, and pharmaceutically-acceptable acid addition salts thereof.

2. A compound according to claim 1 in which both $R^1$ and $R^2$ are methyl, said compound being 1,3-dimethyl-6,7-dimethoxy-1H-1,2,4-benzothiadiazine-1-oxide.

3. The hydrochloride salt of the compound of claim 2.

4. A compound according to claim 1 in which $R^1$ is isopropyl and $R^2$ is methyl, said compound being 1-isopropyl-3-methyl-6,7-dimethoxy-1H-1,2,4-benzothiadiazine-1-oxide.

5. The hydrochloride salt of the compound of claim 4.

6. A compound according to claim 1 in which $R^1$ is isopropyl and $R^2$ is ethyl, said compound being 1-isopropyl-3-ethyl-6,7-dimethoxy-1H-1,2,4-benzothiadiazine-1-oxide.

7. The hydrochloride salt of the compound of claim 6.

8. The method of reducing blood pressure in a mammal with elevated blood pressure and in need of treatment which comprises administering a hypotensive dose of a compound according to claim 1 sufficient to lower said elevated blood pressure in said hypertensive mammal.

* * * * *